US008026221B2

(12) United States Patent
Jiang et al.

(10) Patent No.: US 8,026,221 B2
(45) Date of Patent: Sep. 27, 2011

(54) METHOD, COMPOSITION AND KIT FOR ANTIGENIC BINDING OF NORWALK-LIKE VIRUSES

(75) Inventors: Xi Jiang, Cincinnati, OH (US); Jacques Le Pendu, Nantes (FR)

(73) Assignees: Children's Hospital Medical Center, Cincinnati, OH (US); INSERM, Nantes Codex (FR)

(*) Notice: Subject to any disclaimer, the term of this patent is extended or adjusted under 35 U.S.C. 154(b) by 23 days.

(21) Appl. No.: 12/040,530

(22) Filed: Feb. 29, 2008

(65) Prior Publication Data

US 2008/0274984 A1 Nov. 6, 2008

Related U.S. Application Data

(63) Continuation of application No. 10/520,087, filed as application No. PCT/US03/17247 on Jun. 2, 2003, now abandoned.

(60) Provisional application No. 60/385,283, filed on May 31, 2002, provisional application No. 60/385,296, filed on May 31, 2002.

(51) Int. Cl.
*A61K 31/702* (2006.01)
*C07H 15/04* (2006.01)
*C07H 15/06* (2006.01)
*C07H 5/04* (2006.01)

(52) U.S. Cl. ................ 514/25; 514/53; 514/54; 514/61; 536/17.9; 536/55.1; 536/55.2; 536/123; 536/123.1

(58) Field of Classification Search ........................ None
See application file for complete search history.

(56) References Cited

U.S. PATENT DOCUMENTS

| | | | |
|---|---|---|---|
| 4,916,213 | A | 4/1990 | Scannon et al. |
| 5,254,342 | A | 10/1993 | Shen et al. |
| 5,326,857 | A | 7/1994 | Yamamoto et al. |
| 5,338,689 | A | 8/1994 | Yves et al. |
| 5,559,014 | A | 9/1996 | Estes et al. |
| 5,589,453 | A | 12/1996 | Greve |
| 5,643,579 | A | 7/1997 | Hung et al. |
| 5,665,534 | A | 9/1997 | Vandenbergh et al. |
| 5,750,394 | A | 5/1998 | Palese et al. |
| 5,783,193 | A | 7/1998 | Michael et al. |
| 5,786,340 | A | 7/1998 | Henning et al. |
| 5,789,230 | A | 8/1998 | Cotten et al. |
| 5,861,241 | A | 1/1999 | Herrmann et al. |
| 6,045,854 | A | 4/2000 | Prieto et al. |
| 6,130,205 | A | 10/2000 | Stapleton et al. |
| 6,140,043 | A | 10/2000 | Dierich et al. |
| 6,156,883 | A | 12/2000 | Estes et al. |
| 6,187,762 | B1 | 2/2001 | Mandeville, III et al. |
| 6,254,867 | B1 | 7/2001 | Reisner et al. |
| 6,258,789 | B1 | 7/2001 | German et al. |
| 6,300,090 | B1 | 10/2001 | Steinman et al. |
| 2002/0019991 | A1 | 2/2002 | Prieto et al. |

FOREIGN PATENT DOCUMENTS

WO WO03/003985 * 1/2003

OTHER PUBLICATIONS

Merriam-Webster's Collegiate Dictionary, Tenth Edition copyright 1998 by Merriam-Webster, Incorporated, p. 924.*
Kurdyashov et al., "Characterization of a mouse monoclonal IgG3 antibody to the tumor-associated globo H structure produced by immunization with a synthetic glycoconjugate" Glycoconjugate Journal (1998) vol. 15 pp. 243-249.*
Silverman, "The Organic Chemistry of Drug Design and Drug Action" Published 1992 by Academic Press, pp. 4-47.*
Marionneau et al., "Norwalk Virus Binds to Histo-Blood Group Antigens Present on Gastroduodenal Epithelial Cells of Secretor Individuals" Gastroenterology (2002) vol. 122, pp. 1967-1977.*
Oriol, R. et al., Insights into the Expression of ABH and Lewis Antigens through Human Bone Marrow Transplantation, Am Journal Hum Genet, vol. 33, 1981, pp. 551-560.
Pelosi, E. et al., The seroepidemiology of genogroup 1 and genogroup 2 Norwalk-like viruses in Italy, Journal of Medical Virology, Apr. 1, 1999, vol. 58, Issue 1, pp. 93-99, Abstract.
"Sixth International Symposium" on Positive Strand RNA Viruses (May 29, 2001), Institut Pasteur, Paris, France; Scientific Program Abstracts "Norwalk Virus Binds to H Type I Histo-Blood Group Antigen Present on Gastro-Duodenal Epithelial Cells of "Secretor" Phenotype Individuals", Abstract (2 pages).
Adler, P. et al., High Affinity Binding of the *Entamoeba histolytica* Lectin to Polyvalent N-Acetylgalactosaminides, The Journal of Biological Chemistry, Mar. 10, 1995, vol. 270, No. 10, p. 5164-5171.
Atmar, R. et al., Diagnosis of Noncultivatable Gastroenteritis Viruses, the Human Caliciviruses, Clinical Microbiology Reviews, Jan. 2001, vol. 14, No. 1, p. 15-37.
Brinker, J. P. et al., Immunoglobulin M Antibody Test to Detect Genogroup II Norwalk-Like Virus Infection, Journal of Clinical Microbiology, Sep. 1999, vol. 37, No. 9, p. 2983-2986.

(Continued)

*Primary Examiner* — Eric S Olson
(74) *Attorney, Agent, or Firm* — Hasse & Nesbitt LLC; Daniel F. Nesbitt

(57) ABSTRACT

A method for detecting a Norwalk-Like Virus (NLV) in a biological sample, comprising the steps of: obtaining a biological sample suspected of containing a NLV; contacting the biological sample with at least one human histo-blood group antigen to allow formation of a complex of the NLV with the antigen; and detecting the antigen-NLV complex. The antigen-NLV complex can be detected by contacting the NLV-antigen complex with a NLV antibody that binds at an epitope of the NLV, and detecting the NLV antibody. The invention also includes a method for identifying compounds, and the compounds, that can inhibit the binding between a Norwalk-Like Virus (NLV) and a histo-blood group antigen. The method includes the steps of contacting the NLV target with a compound; subsequently contacting the NLV with a standard compound that is known to be bound at a determinant binding site of the NLV; and determining whether the binding of the standard compound is decreased in the presence of the test compound, the decrease in binding being an indication that the test compound inhibits the binding activity of the NLV with the standard compound. In preferred embodiments, the standard compound is a histo-blood group antigen.

7 Claims, 3 Drawing Sheets

OTHER PUBLICATIONS

Burton-MacLeod, J. A. et al., Evaluation and Comparison of Two Commercial Enzyme-Linked Immunosorbent Assay Kits for Detection of Antigenically Diverse Human Noroviruses in Stool Samples, Journal of Clinical Microbiology, Jun. 2004, vol. 42, No. 6, p. 2587-2595.
Erdman, D. D. et al., Serum Immunoglobulin a Response to Norwalk Virus Infection, Journal of Clinical Microbiology, Jun. 1989, vol. 27, No. 6, p. 1417-1418.
Estes, M. et al., Norwalk Virus Vaccines: Challenges and Progress, The Journal of Infectious Diseases, 2000, 181(Suppl 2), p. S367-S373.
Farkas, T. et al., Homologous versus Heterologous Immune Responses to Norwalk-Like Viruses among Crew Members after Acute Gastroenteritis Outbreaks on 2 Navy Vessels, The Journal of Infectious Diseases, Jan. 2003, vol. 187, p. 187-193.
Farkas, T. et al., Molecular Detection and Sequence Analysis of Human Caliciviruses From Acute Gastroenteritis Outbreaks in Hungary, Journal of Medical Virology, Jan. 2002, vol. 67, p. 567-573.
Gray, J .J. et al., Prevalence of Antibodies to Norwalk Virus in England: Detection by Enzyme-Linked Immunosorbent Assay Using Baculovirus-Expressed Norwalk Virus Capsid Antigen, Journal of Clinical Microbiology, Apr. 1993, vol. 31, No. 4, p. 1022-1025.
Green, K. Y. et al., Taxonomy of Caliciviruses, The Journal of Infectious Diseases, 2000, 181(Suppl 2), p. S322-S330.
Hale, A. D. et al., Expression and Self-Assembly of Grimsby Virus: Antigenic Distinction from Norwalk and Mexico Viruses, Clinical and Diagnostic Laboratory Immunology, Jan. 1999, vol. 6, No. 1, p. 142-145.
Hale, A. D. et al., Identification of an Epitope Common to Genogroup 1 "Norwalk-Like Viruses", Journal of Clinical Microbiology, Apr. 2000, vol. 38, No. 4, p. 1656-1660.
Harrington, P. R. et al., Binding of Norwalk Virus-Like Particles to ABH Histo-Blood Group Antigens is Blocked by Antisera from Infected Human Volunteers or Experimentally Vaccinated Mice, Journal of Virology, Dec. 2002, vol. 76, No. 23, p. 12335-12343.
Harrington, P. R. et al., Norovirus Capture with Histo-Blood Group Antigens Reveals Novel Virus-Ligand Interactions, Journal of Virology, Mar. 2004, vol. 78, No. 6, p. 3035-3045.
Hennessy, E. P. et al., Norwalk Virus Infection and Disease Is Associated with ABO Histo-Blood Group Type The Journal of Infectious Diseases, 2003, 188, p. 176-177.
http://acronyms.thefreedictionary.com/kit, cited as searched on Feb. 18, 2008 by Examiner in corresponding U.S. Appl. No. 11/264,992, printed on Feb. 22, 2008, p. 1-4.
http://encyclopedia.thefreedictionary.com/assay, cited as searched on Feb. 18, 2008 by Examiner in corresponding U.S. Appl. No. 11/264,992, printed on Feb. 22, 2008, p. 1-5.
Huang, P. et al., Noroviruses Bind to Human ABO, Lewis, and Secretor Histo-Blood Group Antigens: Identification of 4 Distinct Strain-Specific Patterns, The Journal of Infectious Diseases, Jul. 1, 2003, vol. 188, p. 19-31.
Huang, P. et al., Norovirus and Hista-Blood Group Antigens: Demonstration of a Wide Spectrum of Strain Specificities and Classification of Two Major Binding Groups among Multiple Binding Patterns, Journal of Virology, Jun. 2005, vol. 79, No. 11, p. 6714-6722.
Hutson, A. M. et al., Norwalk Virus-Like Particle Hemagglutination by Binding to H Histo-Blood Group Antigens, Journal of Virology, Jan. 2003, vol. 77, No. 1, p. 405-415.
Hutson, A. M. et al., ABO Phenotype Association with Norwalk Virus Infection and Disease May Be Related to Norwalk Virus-Like Particle Binding H Antigens, Gastroenterology, vol. 122, No. 4 (Suppl 1), Apr. 2002, pp. A-141, XP009054158 & Digestive Disease Week and the 103rd Annual Meeting of the American Gastroenterological Association, San Francisco, CA, USA, May 19-22, 2002, Abstract.
Hutson, A. M. et al., Norwalk Virus Infection and Disease Is Associated with ABO Histo-Blood Group Type, The Journal of Infectious Diseases, 2002, 185, p. 1335-1337.
Jiang, X. et al., Baculovirus expression and antigenic characterization of the capsid proteins of three Norwalk-like viruses, Archives of Virology, 2002, vol. 147, p. 119-130.
Jiang, X. et al., Expression, Self-Assembly, and Antigenicity of a Snow Mountain Agent-Like Calicivirus Capsid Protein, Journal of Clinical Microbiology, Jun. 1995, vol. 33, No. 6, p. 1452-1455.
Jiang, X. et al., Expression, Self-Assembly, and Antigenicity of the Norwalk Virus Capsid Protein, Journal of Virology, Nov. 1992, vol. 66, No. 11, p. 6527-6532.
Jiang, X. et al., Human Milk Contains Elements That Block Binding of Noroviruses to Human Histo-Blood Group Antigens in Saliva, The Journal of Infectious Diseases, Nov. 15, 2004, vol. 190, p. 1850-1859 (electronically published Oct. 11, 2004).
Jiang, X. et al., Norwalk Virus Genome Cloning and Characterization, Science, Dec. 14, 1990, vol. 250, p. 1580-1583.
Jiang, X. et al., Sequence and Genomic Organization of Norwalk Virus, Virology, 1993, vol. 195, p. 51-61.
Kumar, S. et al., MEGA2: molecular evolutionary genetics analysis software, Bioinformatics Applications Note, 2001, vol. 17, No. 12, p. 1244-1245.
Lew, J. F. et al., Molecular Characterization of Hawaii Virus and Other Norwalk-Like Viruses: Evidence for Genetic Polymorphism among Human Caliciviruses, The Journal of Infectious Diseases, Mar. 1994, vol. 170, p. 535-542.
Lindesmith, L. et al., Human susceptibility and resistance to Norwalk virus infection, Nature Medicine, May 2003, vol. 9, No. 5, p. 548-553.
Marionneau, S. et al., ABH and Lewis histo-blood group antigens, a model for the meaning of oligosaccharide diversity in the face of a changing world, Biochimie 83, 2001, p. 565-573.
Marionneau, S. et al., Norwalk Virus Binds to Histo-Blood Group Antigens Present on Gastroduodenal Epithelial Cells of Secretor Individuals, Gastroenterology, 2002, vol. 122, No. 7, p. 1967-1977.
Nicholas, K. B. et al., GeneDoc: Analysis and Visualization of Genetic Variation, http://www.psc.edu/biomed/genedoc/ebinet.htm, p. 1-5, (2005).
Pelosi, E. et al., The seroepidemiology of genogroup 1 and genogroup 2 Norwalk-like viruses in Italy, Journal of Medical Virology, Apr. 1, 1999, vol. 58, Issue 1, p. 93-99, Abstract.
Prasad, B.V. Venkataram et al., X-Ray Crystallographic Structure of the Norwalk Virus Capsid, Science, Oct. 8, 1999, vol. 286, p. 287-290.
"Sixth International Symposium" on Positive Strand RNA Viruses (May 28-Jun. 2, 2001), Institut Pasteur, Paris, France; Scientific Program Abstracts "Norwalk Virus Binds to H Type I Histo-Blood Group Antigen Present on Gastro-Duodenal Epithelial Cells of "Secretor" Phenotype Individuals", Abstract (2 pages).
Tamura, M. et al., Interaction of Recombinant Norwalk Virus Particles with the 105-Kilodalton Cellular Binding Protein, a Candidate Receptor Molecule for Virus Attachment, Journal of Virology, Dec. 2000, vol. 74, No. 24, p. 11589-11597.
Tan, M. et al., *E. coli*-Expressed Recombinant Norovirus Capsid Proteins Maintain Authentic Antigenicity and Receptor Binding Capability, Journal of Medical Virology, 2004, vol. 74, p. 641-649.
Tan, M. et al., Mutations within the P2 Domain of Norovirus Capsid Affect Binding to Human Histo-Blood Group Antigens: Evidence for a Binding Pocket, Journal of Virology, Dec. 2003, vol. 77, No. 23, p. 12562-12571.
Tan, M. et al., The P Domain of Norovirus Capsid Protein Forms Dimer and Binds to Histo-Blood Group Antigen Receptors, Journal of Virology, Jun. 2004, vol. 78, No. 12, p. 6233-6242.
Tan, M. et al., Norovirus and its histo-blood group antigen receptors: an answer to a historical puzzle, TRENDS in Microbiology, Jun. 6, 2005, vol. 13, No. 6, p. 285-293 (available online Apr. 30, 2005).
Tan, M. et al., The P Domain of Norovirus Capsid Protein Forms a Subviral Particle That Binds to Histo-Blood Group Antigen Receptors, Journal of Virology, Nov. 2005, vol. 79, No. 22, p. 14017-14030.
Treanor, J. J. et al., Development of an enzyme immunoassay for the Hawaii agent of viral gastroenteritis, Journal of Virological Methods, 1988, p. 207-214.
White, L. J. et al., Attachment and Entry of Recombinant Norwalk Virus Capsids to Cultured Human and Animal Cell Lines, Journal of Virology, Oct. 1996, vol. 70, No. 10, p. 6589-6597.
Wobus, C. E. et al., Replication of Norovirus in Cell Culture Reveals a Tropism for Dendritic Cells and Macrophages, PLoS Biology, Dec. 2004, vol. 2, Issue 12, p. 0001-0009.
Jiang et al., U.S. Appl. No. 11/264,992, filed Nov. 2, 2005.
Jiang et al., U.S. Appl. No. 11/940,794, filed Nov. 15, 2007.

* cited by examiner

METHOD, COMPOSITION AND KIT FOR ANTIGENIC BINDING OF NORWALK-LIKE VIRUSES

CROSS REFERENCE TO RELATED APPLICATIONS

This application is a continuation of U.S. application Ser. No. 10/520,087, filed Dec. 28, 2004 now abandoned which was the National Stage of International Application No. PCT/US03/17247, filed Jun. 2, 2003, which claimed the benefit of Provisional Application No. 60/385,283, filed on May 31, 2002 and U.S. Provisional Application No. 60/385,296, filed on May 31, 2002.

INTERESTS

This invention was made with Government support by the U.S. National Institutes of Health (National Institute of Allergy and Infectious Diseases, grant RO1 AI37093 and National Institute of Child Health and Human Development, grant HD13021). The Government has certain rights in this invention.

FIELD OF THE INVENTION

The present invention relates to Norwalk-Like Viruses, to their recognition of and binding to human histo-blood group antigens, and to a compound and a method of screening for the compound that can inhibit binding between a Norwalk-Like Virus and a human histo-blood group antigen.

BACKGROUND OF THE INVENTION

The Norwalk-Like Viruses (NLV), now are called Noroviruses, are small round viruses within the calicivirus family and are important viral pathogens that cause acute gastroenteritis, the second most common illness in the United States. Norwalk disease is a mild to moderate illness that develops 1-2 days after infection by person-to-person transmission, surface contamination, or by contaminated food or water and the illness lasts for 24-60 hours. Symptoms include nausea, vomiting, diarrhea, abdominal pain and upon occasion headache and low fever. Severe illness requiring hospitalization is most unusual. Particularly large epidemic outbreaks of illness have occurred following consumption of contaminated water or uncooked food such as salad and ham, and shellfish including clams, cockles, and oysters.

NLVs are morphologically similar but genetically and antigenically diverse viruses. Genetically, NLVs belong to one of two genera, the "Norwalk-like viruses" (NLVs) and the "Sapporo-like viruses" of human caliciviruses, a subset of *Caliciviridae*. The NLV genus can be divided into three genogroups (I, II, and III). Each genogroup can be further divided into genetic clusters; at least 15 genetic clusters of NLVs have been identified (see *Capsid protein diversity among the Norwalk-like viruses*, Virus Genes 2000; 20:227-36, incorporated herein by reference.) NLVs encode a single capsid protein that self-assembles into virus-like particles (VLPs) when the recombinant capsid protein is expressed in baculovirus-infected insect cells (see *Expression, self-assembly, and antigenicity of the Norwalk virus capsid protein*, Jiang at al., Journal of Virology, 66:6527-32 (1992), incorporated herein by reference). These VLPs are morphologically and immunologically indistinguishable from the authentic viruses found in human feces.

Since the molecular cloning of NLVs and the subsequent development of new diagnostic assays, NLVs have been recognized as the most important cause of non-bacterial epidemics of acute gastroenteritis in both developed and developing countries, affecting individuals of all ages. Over 90% of non-bacterial gastroenteritis outbreaks in the US are found to be associated with NLVs. The percentage of individuals in developing countries who have antibodies against NLVs at an early age is very high (as it is with poliovirus and other viruses transmitted by fecal contamination of water and foods). In the US the percentage increases gradually with age, reaching 50% in people over 18 years of age. The antibody prevalence to NLVs is estimated to be higher based on the data using new diagnostic methods than previously reports using old methods. Immunity, however, is not permanent and reinfection can occur.

Before molecular cloning of NV in 1990, several methods were developed for diagnosis of Norwalk virus that included immune electron microscopy and other immunologic methods such as radio immunoassays (RIAs) or enzyme linked immunoabsorbent assays (ELISAs). Because most of these methods use reagents from infected humans that are of limited source, they are not widely used. Since the molecular cloning of NLVs, several methods have been developed for diagnosis of NLVs, including reverse transcription-polymerase chain reaction (RT-PCR) for detection of the viral RNA and recombinant enzyme immune assay for detection of viral antigens and antibody against viral antigens. Due to the wide genetic and antigenic diversity of NLVs, these methods encountered problems of low detection sensitivity and specificity.

Although the Norwalk Virus was discovered in 1972, knowledge about the virus has remained limited because it has failed to grow in cell cultures and no suitable animal models have been found for virus cultivation. Human stool samples obtained from outbreaks and from human volunteer studies, therefore, are the only source of the virus. Still the concentration of the virus in stool is usually so low that virus detection with routine electron microscopy is not possible. Although limited studies on human volunteers showed that antibody response to NV challenge was protective against subsequent infection, other studies found that pre-existing antibodies against NV were not protective. Even more puzzling has been that some individuals with high levels of antibody against NV were more susceptible to the virus than individuals who did not have the antibody, and that 20-30% of individuals who did not have antibody against NV could not be infected by challenge with NV.

The most commonly encountered blood groups are ABO (ABH) and Lewis. (See Hematology Basic Principles and Practice, R. Hoffman, editor; Churchill Livingstone NY, N.Y., pub. 1995). The biosynthetic pathways used in forming antigens in the ABH, Lewis, P, and I blood group systems are interrelated. These oligosaccharide antigens may exist free in solution. In addition, they can be covalently attached to lipid molecules (ceramide) to form glycosphingolipids, or to polypeptides to form mucins, integral membrane glycoproteins, or soluble glycoproteins. The lycosidic linkages (i.e., the bonds between monosaccharides) are specifically catalyzed by glycosyltransferases. Some glycosyltransferases, found in all individuals, form framework structures. Other glycosyltransferases are allelically inherited and specify the synthesis of variable structures. Because of their variable inheritance and expression, the latter may form blood group antigens. As described below, antigens in the ABH, Lewis, P, and I blood group systems are synthesized on common precursor framework molecules. Competition between genetically inherited blood group-specific glycosyltransferases results in a rich mixture of antigenic molecules. In addition, a single oligosaccharide may contain several different blood group specificities. The absence of particular blood group antigens in certain individuals may result in specific antibody production after antigenic stimulation.

Although the ABH antigens are typically described as blood group antigens because of their presence on red cells, they are also found on other tissues, and may be more appropriately termed histo-blood group antigens. In blood, they exist in both a cellular form on platelets and a soluble form as blood group active glycosphingolipids coupled to plasma lipoproteins. They exist as membrane antigens on such diverse cells as vascular endothelial cells and intestinal, cervical, urothelial, pulmonary and mammary epithelial cells. Soluble forms are also found in various secretions and excretions, such as saliva, milk, urine, and feces. In some tissues, their appearance is developmentally regulated. Despite their wide distribution, genetic inheritance, developmental regulation, and importance in transfusion and transplantation, their normal physiological function, if any, remains a mystery.

To appreciate the structure and antigenicity of ABH antigens and their relationship to other blood group systems fully, it is necessary to understand the underlying biochemistry.

Early studies indicated that anti-A, anti-B, and anti-H antibodies specifically recognize epitopes composed of terminal trisaccharides or disaccharides. From these results it is possible to conclude that the A, B, and H antigens are not directly encoded by the corresponding genes, but rather the genes code for particular glycosyltransferases, commonly called the A, B, and H transferases, or equivalently, the A, B, and H enzymes. The H enzyme is a fucosyltranferase that specifically adds fucose in an ($\alpha$-1→2) linkage to a terminal galactose. The A or B enzymes then add N-acetylgalactosamine or galactose, respectively, in an ($\alpha$-1→3) linkage to the same terminal galactose. However, the substrate for the A or B enzymes is a terminal H antigen; these enzymes do not transfer the appropriate sugar to galactose in the absence of the ($\alpha$-1→2)-linked fucose. Similarly, the H enzyme does not function if this galactose is substituted with a different sugar.

The finding that the A and B genes code for glycosyltransferases explains some results obtained from classic genetic analysis of family pedigrees. In particular, the A and B genes are inherited in a strict mendelian fashion and are dominant compared to O, but the A and B genes are co-dominant with each other. That is, an individual with the genotype AO (or BO) is phenotypically A (or B), an individual of genotype OO is phenotypically group O. Since the A and B enzymes both use the H antigen as substrate, even the presence of only approximately 50% of these enzymes in and AO (or BO) heterozygote is sufficient to convert the red cells to the corresponding A (or B) phenotype. Similarly, if both the A and B enzymes are present, they each convert approximately 50% of the available H antigen substrate, yielding red cells expressing both antigens A and B.

The ABH antigens are found not only on cells but also in secretions, particularly saliva and plasma. The ability to secrete ABH is genetically inherited: approximately 80% of whites are secretors and 20% are nonsecretors. This trait is inherited as a single locus gene (FUT2) in simple mendelian fashion. The secretor gene (Se) is dominant; nonsecretor (se) is recessive. The terminal carbohydrate sequences of the ABH antigens in saliva and plasma are identical to those on red cells. At least one copy of the Se gene is found in approximately 80% of the population and leads to the expression of ABH antigens in secretions. By contrast, the traditional H locus is a structural gene called FUT1. This gene is active in virtually all individuals, with rare defective mutation such as the "Bombay" blood type, and leads to the formation of ABH antigens on red blood cells and other tissues.

The two Lewis blood group antigens $Le^a$ (Lewis a) and $Le^b$ (Lewis b) were discovered in the 1940s. Virtually all individuals fall into one of three different Lewis types Le(a+b−), Le(a−b+), and Le(a−b−). A type of Le(a+b+) is seen among Asian populations. These molecules are not intrinsic red blood cell antigens; they are synthesized in another tissue (probably the intestinal epithelium), circulate in plasma attached to lipoproteins, and then passively transfer onto red cells. Biochemical studies have demonstrated that these are carbohydrate antigens on glycosphingolipids. They are structurally similar to the type ABH antigens found on plasma glycosphingolipids that likewise transfer onto red blood cells. The Lewis gene codes for an enzyme, an ($\alpha$-1→4) fucosyltransferase, and thus behaves in a dominant fashion. The transfer of fucose to a type 1 precursor by the Lewis enzyme results in the formation of the $Le^a$ antigen; the addition of ($\alpha$-1→4) linked fucose to the H type 1 structure leads to the formation of the $Le^b$ antigen. Thus the $Le^b$ antigen is formed through the cooperation of two glycosyltransferases encoded by two genes, one gene for the Lewis system (Le) and one from the ABH system (Se) or, equivalently, H type 1 at a different, unlinked locus, demonstrating the connections of the ABH, Secretor, and Lewis systems. Since the secretor enzyme converts virtually all type 1 precursor into H type 1, whether or not the Lewis enzyme is present, Lewis-positive secretors have virtually no $Le^a$ antigen, and their red blood cells type as Le(a−b+). By contrast Lewis-positive nonsecretors have Le(a+b−) red blood cells.

Histo-blood group antigens have been linked to infection by several bacterial and viral pathogens. This suggests that the histo-blood group antigens are a recognition target for pathogens and may facilitate entry into a cell that expresses or forms a receptor-ligand bond with the antigens. While the exact nature of such an interaction is unknown, close association of a pathogen that would occur with antigen binding may play a role in anchoring the pathogen to the cell as an initial step in the infection process. Interactions of some parasites and bacteria with human cells have been shown to depend on the presence of certain blood group antigens. For example, *P. vivax* malarial parasites only enter human red blood cells when the Fy6 Duffy blood group protein is present on the cells. Certain *E. coli* will only attach to the epithelial cells of the urinary tract if P or Dr blood group antigens are present in the epithelial cells. The P antigen is also the red blood cell receptor for Parvovirus B19. $Le^b$ antigen has recently been found to be the receptor for *H. pylori* in the gastric tissue. The high frequency blood group antigen known as AnWj, is the red blood cell receptor for *H. influenzae*. Since the relevance of ABH blood group antigens as parasitic/bacterial/viral receptors and their association with immunologically important proteins is now well established, the prime biologic role for ABH blood group antigens may well be independent and unrelated to the erythrocyte.

A recent study has shown that a relationship may exist between a person's ABO histo-blood group type and the risk of an infection and symptomatic disease after clinical challenge by the Norwalk Virus (NV). (See *Norwalk Virus Infection and Disease is Associated with ABO-Histo-Blood Group Type*, The Journal of Infectious Diseases, 185:1335-7 (2002), incorporated herein by reference). The study shows that persons of blood type O were significantly more likely to become infected with the NV, while persons of blood type B and AB had a decreased risk of infection, and that blood type B persons did not develop symptomatic illnesses despite being challenged with the NV.

Despite the advances made in recognizing that human histo-blood type may affect the risk of infection by the Norwalk Virus, there has been no explanation of the specific binding mechanism used by NLVs to infect human epithelium cells in the gastrointestinal (GI) tract, and no explanation of the specific binding relationships between NLVs, including the NV, and the human histo-blood group antigens. Furthermore, there has not been shown an effective means to treat a NLV infection and/or its illness.

Therefore, the need has remained to understand: the specific mechanism for NLV infection within the GI tract, the specific binding properties of the prototype NV with the ABO blood antigens and the Le blood antigens, the specific binding properties of the other NLVs with the human histo-blood phenotypes and their respective blood antigens, and the compounds and compositions that are effective to inhibit binding between NLVs and blood antigens, to prevent or treat an infection by a NLV and/or the resulting illness.

SUMMARY OF THE INVENTION

The present invention follows from the discoveries that the various NLV virus like particles (VLPs) can recognize and bind to one or more human ABH and Lewis histo-blood group antigens, and that a human histo-blood group antigen can recognize and bind to one or more NLVs, in varied blood antigen-NLV binding patterns. The invention predicts that NLVs can infect humans who have a human histo-blood type that presents blood antigens that can bind the particular strain of infecting NLVs. The invention also predicts that a strain of NLV will bind with one or more histo-blood group antigens, but will not bind with all other blood group antigens.

A first aspect of the invention relates to a method for determining if a person has been infected with a NLV, by using at least one blood antigen, to complex with and detect the NLV. The method for detecting a NLV in a biological sample, comprises the steps of a) obtaining a biological sample suspected of containing a NLV; b) contacting the biological sample with at least one blood antigen target to allow formation of a complex of the NLV with the blood antigen; and c) detecting the NLV-blood antigen complex.

The kit comprises an assay for detecting a NLV in a biological sample, comprising a) a container for holding a biological sample suspected of containing a NLV, the container comprising a media having affixed at least one blood antigen capable of complexing with a NLV; and b) an assay for the detection of a complex of the NLV and blood antigen.

A second aspect of the invention relates to a method for detecting a histo-blood group antigen in a biological sample, comprising the steps of a) obtaining a biological sample containing a histo-blood group antigen preferably selected from ABH type antigens, Lewis type antigens, and mixtures thereof; b) contacting the biological sample with at least one NLV target to allow formation of a complex of the blood antigen with the NLV; and c) detecting the blood antigen-NLV complex.

A third aspect of the invention relates to a kit that comprises an assay for use in determining the histo-blood group of a human, comprising a) a container for holding a biological sample from a human, the container comprising a media containing at least one NLV capable of complexing with an histo-blood group antigen; and b) an assay for the detection of a complex of the at least one NLV and the blood antigen.

A fourth aspect of the invention relates to a method of identifying a compound that inhibits the binding activity of a NLV VLP toward a human histo-blood antigen. The invention further relates to a first test compound that can competitively bind the determinant binding site of a NLV, or that can bind to an epitope of a NLV, whereby a histo-blood group antigen is prevented from binding at the determinant binding site of the NLV. A preferred first test compound comprises a binding site that binds to a NLV with the binding specificity of the antigenic determinant epitope of the human histo-blood group antigen.

A fifth aspect of the invention relates to a method of identifying a compound that inhibits the binding activity of a human histo-blood antigen toward a NLV. The invention also relates to a second test compound that can competitively bind the antigenic determinant epitope of a human histo-blood group antigen, or that can bind an epitope of a human histo-blood group antigen, whereby a NLV is prevented from binding at the antigenic determinant epitope of a human histo-blood group antigen. A preferred second test compound comprises a binding site that binds to a human histo-blood group antigen with the binding specificity of the determinant binding site of the NLV.

A sixth aspect of the invention relates to a pharmaceutical composition or a medicament that comprises a first compound of the present invention, that can competitively bind to a NLV to inhibit its binding to a human histo-blood antigen, and/or a second compound that can bind to a human histo-blood antigen to inhibit its binding to a NLV.

A seventh aspect of the invention relates to the use of a compound that has the binding specificity of the antigenic determinant of a human histo-blood group antigen in a medicament or pharmaceutical for the prevention and treatment in a mammal of an infection by a NLV.

An eighth aspect of the invention relates to kits and assays for use with the methods and for administering the first and/or second compounds of the present invention.

DETAILED DESCRIPTION OF THE INVENTION

Definitions

Figure 1:
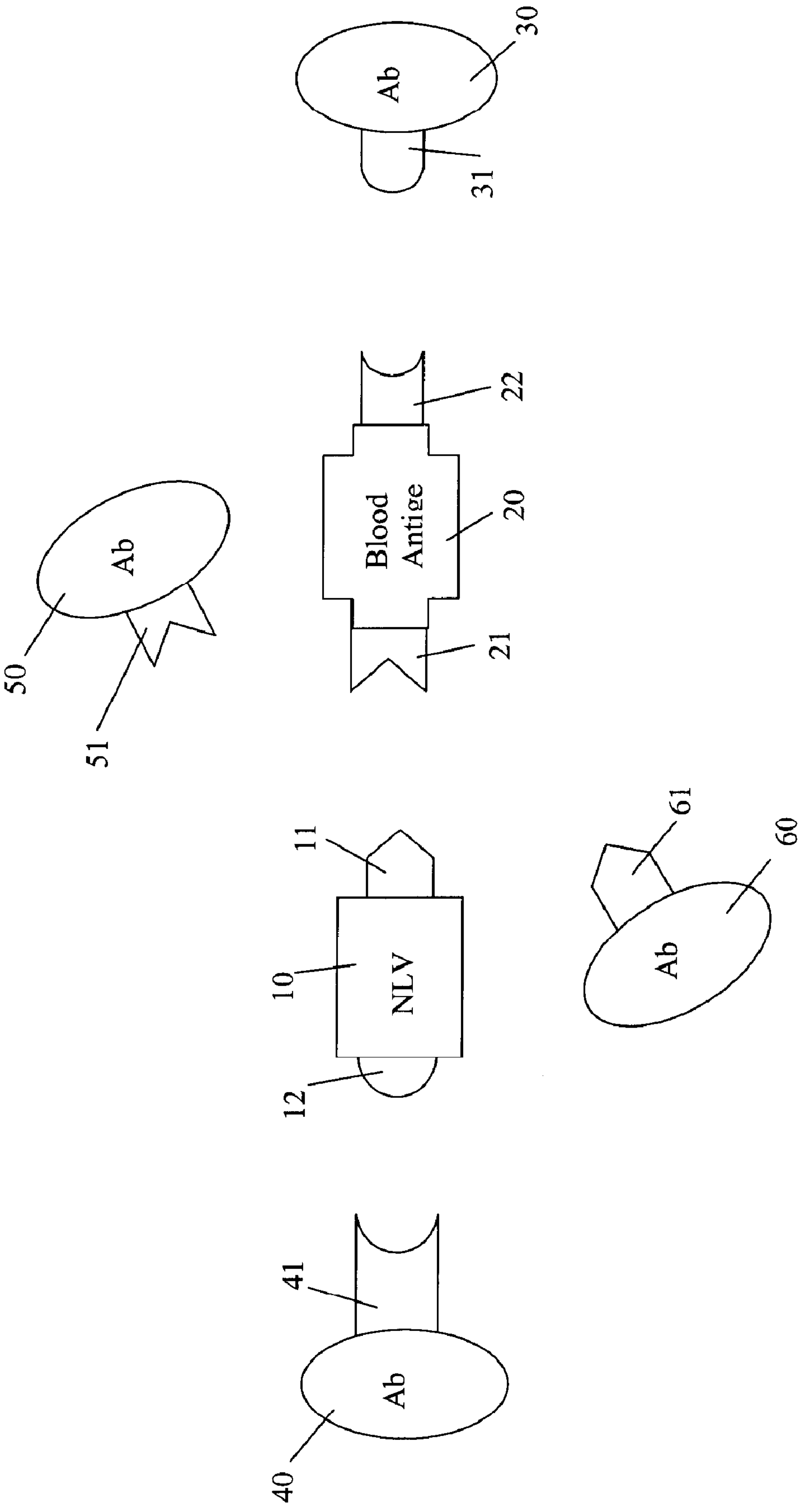
FIG. 1 shows simplified models of a NLV and a blood antigen, with their respective binding sites and epitopes, and antibodies and compounds for binding to the NLV and blood antigen with their respective binding sites.

As used herein, the term "infect" refers to the process by which a virus, such as a NLV, releases its genome into a cell. In most cases, the process of "infection" causes the cell to replicate the viral genome and produce multiple daughter copies of the parental "infecting" virus.

As used herein, the term "functionally equivalent molecule" means one that can adequately substitute for a compound it is meant to mimic by supplying a function equivalent to the function of the compound. The function that is supplied can include, but is not limited to, the binding specificity of a binding site, an epitope, an active site, a catalytic site, or a recognition site or any combination thereof. A functionally equivalent molecule can substitute for more that one compound, thus combining or providing multiple functions. A functionally equivalent molecule can be a synthetic analog or a naturally occurring compound or portion of a compound. For example, a specific functional domain of a naturally occurring compound can be enzymatically cleaved from the native compound and purified for use. Alternatively, such a domain can be expressed as a recombinant protein in a suitable host and purified for use.

As used herein, the term "biological sample" means one that is obtain from the body fluids or cells of an organism. Examples of an organism include any mammal, and in particular refer to humans, mice, rats, rabbits, goats, guinea pigs, and donkeys. Examples of body fluids include but are not limited to blood, plasma, serum, or mucosal fluids, and secreted body fluids such as saliva.

As used herein, the term "incubation" means an interval of time for which an experimental procedure or reaction is allowed to occur. An incubation interval may also be defined as a specified interval of time and a specified temperature at which a biological reaction may be expected to occur.

As used herein, the term "optimiz(e, ing, ation)" refers to the empirical experimental process of determining the best conditions at which a biological reaction or series of reactions will occur. Components of the optimization process can include but are not limited to determining the most advantageous incubation time, temperature, chemical constituents, exposure to light, pH, concentrations of the chemical and biological constituents, and especially combinations of these components, in order to achieve an experimental outcome.

As used herein the term "Norwalk-Like Virus" or "NLV" means any virus of the NLV family, and includes, without limitation, the following: Norwalk Virus, MOH, Mexico, VA 207, VA 387, 02-1419, C59, VA 115, Hawaii, Snow Mountain, Hillington, Toronto, Leeds, Amsterdam, Idaho Falls, Lordsdale, Grimsby, Southampton, Desert Shield, Birmingham, and White Rivercap.

Each histo-blood group antigen can bind to the NLV VLP of one, and usually to at least 2, NLVs. Conversely, each NLV will bind to at least one, and usually with 2 or more blood antigens. The blood antigen binds to the NLV at the blood antigen's antigenic-determinant epitope (the sugar moiety). The NLV binds to the blood antigen at the determinant binding site on the VLP's protein structure. The group of blood antigens to which a NLV will bind is referred to as that NLV's antigen binding pattern.

FIG. 1 shows various simplified models of a NLV 10, a histo-blood antigen 20, and binding compounds, including antibodies (Ab) or other compounds 30, 40, 50 and 60, for binding with the NLV or antigen. For illustration, the description immediately hereafter refers to such binding compounds as antibodies, although such binding compounds can also comprise a natural or synthetic compound that can bind with either a NLV or a histo-blood antigen. The NLV 10 comprises a determinant binding site 11 that binds specifically with an antigenic determinant epitope 21 of the blood antigen 20. Blood antigen 20 can be described as being in the NLV's binding pattern, and visa versa. The blood antigen 20 also has at least one non-determinant epitope 22 that can no bind with the NLV 10, but that can be bound by a non-determinant binding site 31 of an antigen antibody 30. NLV 10 also has at least one NLV epitope 12 that can not bind with the blood antigen 20, but that can be bound by a NLV binding site 41 of a NLV antibody 40. The antibodies 30 and 40 are generally referred to as detection or detectable antibodies for the blood antigen and NLV, and are generally monoclonal antibodies that can be isolated and that have specificity to counter-part epitopes on the blood antigens and NLV. In addition, the binding site 11 of NLV 10 can also bind to an anti-NLV epitope 51 of an anti-NLV antibody 50, with the same binding specificity as with epitope 21 of the blood antigen 20; and the epitope 21 of the blood antigen 20 can be bound by the anti-antigen binding site 61 of an anti-antigen antibody 60, with the same binding specificity as with binding site 11 of the NLV 10. Antibody 50 can bind with NLV 10, or antibody 60 can bind with blood antigen 20, thereby inhibiting the binding between NLV 10 and blood antigen 20.

Five NLV strains have been shown to provide a specific pattern of binding with one or several of the five blood antigens: the H antigen, the A antigen, the B antigen, the $Le^a$ antigen and the $Le^b$ antigen. These five virus strains are the VA387, MOH, NV, 02-1419, and VA207 viruses. The VA387 strain binds to the A, B, H and $Le^b$ blood antigens, but does not bind to $Le^a$ antigen. The prototype NV strain binds to A, H and $Le^b$ antigens, but does not bind to B or $Le^a$ antigens. Strain 02-1419 binds to A antigen, but does not bind to H, B, $Le^b$, or $Le^a$ antigens. MOH strain binds to A and B antigens, but does not bind to H, $Le^b$, or $Le^a$ antigens. The VA207 strain binds to $Le^a$ antigen, but does not bind to H, A, B or $Le^b$ antigens. Conversely, blood antigen A is bound by the 387, NV, 02-1419, and MOH strains, but not bound by the 207 strain. The blood antigen B is bound by the 387 and MOH strains, but not bound by the NV, 02-1419, and VA207 strains. The blood antigen H and the $Le^b$ antigens are bound by the VA387 and NV strains, but not bound by the MOH, 02-1419, and VA207 strains. The blood antigen $Le^a$ is bound by the VA207 strain, but not bound by the VA387, NV, 02-1419, and MOH strains. These binding patterns are summarized in Table A.

TABLE A

Binding of NLV strains to Human Histo-blood group Antigens

| | Human Histo-Blood Antigen | | | | |
|---|---|---|---|---|---|
| NLV | A | B | H | $Le^b$ | $Le^a$ |
| 387 | B | B | B | B | — |
| NV | B | — | B | B | — |
| MOH | B | B | — | — | — |
| 207 | — | — | — | — | B |
| 02-1419 | B | — | — | — | — |

B = Binding
— = minimal or no binding

Other NLVs among the dozens of known strains can also bind to at least one histo-blood group antigen. Many of these other NLVs will have a similar binding pattern to those above. Other NLVs can have another binding pattern based on the specificity of their determinant binding site for the antigenic determinant epitopes of the blood antigens. From the binding patterns of other NLVs, similar binding tables can be prepared that could show a unique binding pattern with the blood antigens in the respective ABH and Lewis blood groups.

Without being bound by any particular theory, each known NLV has at least one determinant binding site that can be bound by the determinant epitope of at least one of the histo-blood group antigens of the ABH, and Lewis blood groups. Infection of a host by a NLV occurs when a NLV is recognized and bound by a histo-blood group antigen of the host's phenotype. The association of the host's blood antigen with receptors on the epithelial cells of the host brings the NLV into proximity with the epithelial cell. It is believed that this proximity of the NLV to an epithelial cell renders the cell susceptible to infection when the NLV releases its genetic material into the cell. Disruption of the binding between the NLV and the host's blood antigen(s) eliminates the opportunity for the NLV to come into close proximity with the epithelial cells, and diminishes their susceptibility to infection.

It has been shown that some individuals do not become infected when exposed to certain strains of NLVs. In most of these cases, the host does not have a blood antigen that could bind with the particular NLV. Without a host blood antigen to deliver the NL V into proximity with the host's epithelial cells, no infection could occur.

The present invention includes novel methods and kits for detecting a NLV in a biological sample, for detecting histo-blood group antigens in a biological sample, and for a method of screening for the compound that can inhibit binding between a NLV and a human histo-blood group antigen.

Detecting a NLV in a Biological Sample

The present invention can include a method to detect if a person has a Norwalk-Like Virus (NLV) infection. The method can also be used to identify the specific NLV that has infected the person, or to identify that a virus belonging to one of a group of NLVs has infected the person. A person infected with a NLV will generally pass the NLV through the gastrointestinal (GI) tract with the stool, whereby stool sample collected from the infected person will contain the virus. Ordinarily, only a single type of NLV will have infected a person at one time.

The biological sample suspected of containing a NLV, typically a stool sample, is contacted with at least one, and preferably more than one, blood antigen as a target. The blood antigen can be selected from a natural human histo-blood group antigen, a synthetic human histo-blood group antigen, and a functionally equivalent molecule that binds to the NLV with the binding specificity of the human histo-blood group antigen. The functionally equivalent molecule can be an anti-NLV antibody that binds to a determinant binding site of the NLV. The blood antigen is preferably selected from the group consisting of H antigen, A antigen, B antigen, $Le^a$ antigen, $Le^b$ antigen, and mixtures thereof. The natural blood antigen can be obtained from the biological fluids (saliva, blood, etc.) of individuals of that histo-blood group type. For example, $Le^a$ antigen can be obtained from the body fluid (such as saliva) of a person who is a Lewis positive non-secretor. An antigen can be obtained from a person who is a secretor and of type "A" blood; and so forth. A synthetic antigen is a compound selected from a protein, peptide, oligosaccharide, natural compound, and mixtures thereof, that comprises the analog of the antigenic determinant epitope of the natural blood antigen, which can bind to the determinant binding site of a NLV with the binding specificity of the antigenic determinant epitope of the natural human histo-blood group antigen. An example of a synthetic antigen can comprise an oligosaccharide conjugated to BSA, and can include, but is not limited to, A trisaccharide-BSA (GalNAc-α1→3 (Fuc-α1→2) Gal β-O-space) nBSA), B trisaccharide-BSA (Gal-α1→3 (Fuc-α1→2) Gal β-O-space) nBSA), Lacto-N-fucopentaose II-BSA [or, $Lewis^a$ trisaccharide], Lacto-N-fucopentaose I-BSA [or H type 1 trisaccharide], and Lacto-N-difucohexaose I-BSA [or, $Lewis^b$ trisaccharide], available from Glycorex AB, Lund, Sweden, and from V-Labs, Inc., Covington, La.

The binding specificity of synthetic histo-blood antigens (for example, an oligosaccharide conjugated to BSA) with a NLV has been demonstrated wherein a specific synthetic histo-blood antigen (for example, A trisaccharide-BSA) losses binding with a NLV (such as a NV) after digestion to remove the antigenic determinant sugar epitope from the synthetic oligosaccharide with a glycosidase (for example, an α-N-acetylgalactosaminidase for the A trisaccharide-BSA). Thus, the corresponding NLV could not be bound.

The method uses preferably at least 2 and more preferably all of the blood antigens. The plurality of blood antigens is preferably contacted separately to allow the NLV in the biological sample to contact each blood antigen individually. However, a mixture of two or more blood antigens can be placed together into a single area depending on the method of detection and the specificity of detection required.

A complex can form between the NLV and the blood antigen provided that the NLV and the blood antigen have a binding affinity for each other, and that the contacting step provides sufficient incubation time and conditions to form the NLV-blood antigen complex.

The resulting NLV-blood antigen complex is then detected. After the biological sample has been contacted and complexed, the non-binding material of the biological sample is washed from the complex and/or target. The non-binding material includes any NLV that does not bind to the blood antigen target. Detection and identification monoclonal antibodies (MAbs) or polyclonal antibodies can be used for detecting the NLV-blood antigen complex.

The detection can be either a direct detection method or an indirect detection method, or both. The direct detection of a NLV bound to a blood antigen can be made by contacting the NLV-blood antigen complex with a detectable NLV antibody that has a NLV binding site that binds to a non-determinant NLV epitope (i.e., an epitope other than the determinant binding site) of the NLV. After optimized contacting between the complex and the detectable NLV antibody, any unbound NLV antibody is washed away. The NLV antibody is then detected, which determines that a NLV has bound to the blood antigen target. The NLV antibodies can be used one by one to detect whether a specific NLV is present in the complex, or can be used as a group (cocktail) of antibodies to detect whether any one of the group of NLVs is present in the complex.

Detectable NLV antibodies that bind to a determinant or non-determinant NLV epitope of a NLV include rabbit and guinea pig antibodies against NV strain, 387 strain, 207 strain, MOH strain, Mexico strain, 02-1419 strain, and any other NLV strain, respectively.

The indirect detection of a NLV bound to a blood antigen can be made by contacting the blood antigen target with a detectable anti-antigen antibody having an anti-antigen binding site that binds specifically to the antigen-determinant epitope of the blood antigen. After optimized contacting between the target antigen and the detectable anti-antigen antibody, any un-bound anti-antigen antibody is washed away from the blood antigen target. The anti-antigen antibody is then detected, which determines that the anti-antigen antibody has bound to the blood antigen target. If the anti-antigen antibody can not be detected, then one can presume that a NLV has bound to that blood antigen target, and has blocked binding by the anti-antigen antibody. If the detectable anti-antigen antibody can bind to the blood antigen target and is detected, then it can be concluded that a NLV had not bound to antigenic determinant epitope of that blood antigen target.

Detectable anti-antigen antibodies that bind specifically to the antigen-determinant epitope of blood antigen(s) include MAbs BG-4 anti-H type 1, BG-5 anti-$Le^a$, BG-6 anti-$Le^b$, BG-7 anti-$Le^x$, and BG-8 anti-$Le^y$, available from Signet Laboratories, Inc. (Dedham, Mass.), MAbs BCR9031 anti-H type 2, BCR 9010 anti-A, and BCRM 11007 anti-B, available from Accurate Chemical & Scientific Corporation (Westbury, N.Y.), 7-LE anti-$Le^a$, 2-25LE anti-$Le^b$, 19-OLE anti-H type 2, and 3-3A anti-A, available from Dr. J. Baca (Villejuif, FR), and ED3 anti-B available from Dr. A. Martin (Rennes, FR).

Detectable anti-NLV antibodies that binding specifically to NLVs include rabbit and guinea pig hyperimmune antibodies against individual strains of NLVs, and hyperimmune antibodies against a pooled antigens that include, but are not limit to, the NV, VA387, VA207, 02-1419, and MOH. Pooled hyperimmune antibodies are available as Lot # Rabbit 15, Rabbit 16, and Rabbit 17 from Xi Jiang, Children's Hospital Research Center, Cincinnati, Ohio.

The blood antigen can be arranged as targets in discrete areas to determine the binding pattern for the NLV, which can also serve as a confirmation of the identity of the NLV, or class of NLV, since each NLV has a unique binding pattern with the blood antigens.

The invention can also embody a kit for detecting a NLV in a biological sample, comprising: a) a container for holding a biological sample (usually a stool sample from a human that is suspected of containing a NLV, the container comprising a media having thereon affixed at least one blood antigen capable of complexing with a NLV; and b) an assay for the detection of a complex of the NLV blood antigen. The assay can comprise an ELISA that comprises a detectable NLV antibody that has a NLV binding site that binds to a determinant or non-determinant epitope of the NLV of the NLV-blood antigen complex. Since the identity of a NLV in a biological stool sample is usually unknown, a plurality of the detectable NLV antibodies is preferably used. The assay also optionally includes a means for washing away any unbound biological sample and unbound NLV VLPs, and for washing away any unbound detectable NLV antibody from the media. The assay can also comprise an ELISA that comprises an anti-antigen antibody that binds to the antigen-determinant epitope of the blood antigen.

b. Detecting a Histo-Blood Group Antigen in a Biological Sample

The present invention can comprise a method to detect for and determine the blood antigens present in a biological sample.

The biological sample is preferably a saliva sample, which can be obtained in numerous ways. The sample is treated by boiling preferably, to inactivate native antibodies which may interfere with the assays. The treated sample is centrifuged to remove any debris. The supernate of the sample is then collected and stored frozen before use in the test. The biological sample is then contacted with at least one NLV as a target, and incubated to form a complex between a histo-blood group antigen present in the saliva and the NLV. Preferably at least two NLVs are used. Preferably the NLV targets are contacted separately by the saliva sample. The NLV is preferably one that has a known binding pattern for the blood antigens.

The resulting blood antigen-NLV complex is then detected. After the biological sample has been contacted and complexed, the non-binding material of the biological sample is washed from NLV target. The non-binding material includes any blood antigen from the sample that does not bind to the NLV target. Detection and identification hyperimmune or monoclonal antibodies can be used for detecting the blood antigen-NLV complex.

The preferred detection steps comprise contacting the NLV targets with an anti-NLV antibody that binds at a determinant binding site of the respective NLV. After washing away any unbound anti-NLV antibody, any remaining anti-NLV antibody bound to a NLV target is detected. Binding of the anti-NLV antibody to the NLV target indicates that the NLV had not bound to any blood antigens in the sample. Conversely, the absence of binding by the anti-NLV antibody to the NLV target can be presumed to indicate that a blood antigen had already complexed with the NLV target. In a preferred embodiment, the method comprises contacting a saliva sample with separate targets of the NLV strains 387, MOH, NV, 02-1419, and 207. The binding patterns of the anti-NLV antibodies to the NLV targets indicate the NLV-blood antigen binding pattern for the biological sample, and thus the type of blood antigens present in the biological sample. Table B shows the six binding patterns for the histo-blood group antigens with these five NLV strains when detecting with an anti-NLV antibody, and the blood type of the biological sample that corresponds to the binding pattern.

TABLE B

Binding by Anti-NLV Antibody to a NLV target

| | Target NLV | | | | | Biological sample |
|---|---|---|---|---|---|---|
| Pattern no. | 387 | NV | MOH | 02-1419 | 207 | Blood type |
| 1 | — | B | — | b | b | "B secretor" |
| 2 | — | — | — | — | b | "A secretor" |
| 3 | — | — | — | — | b | "AB secretor" |
| 4 | — | — | b | b | b | "O secretor" |
| 5 | b | B | b | b | — | "Le$^a$, Non-secretor" |
| 6 | b | B | b | b | b | "Le$^-$, Non-secretor" |

b = Binding by the anti-NLV antibody
— = minimal or no binding

Other NLV strains can be shown to have specific binding patterns with blood antigens according to the present invention. One or more of the five NLVs in the above example can be replaced with one or more other known NLVs, so long as the cumulative binding patterns can positively identify the blood antigens of the biological sample.

In an alternative embodiment, the method comprises contacting a known NLV with a biological sample target. Detection of the NLV-blood antigen complex can be detected by contacting the biological sample target with a detectable NLV antibody that binds to a determinant or non-determinant epitope of the respective NLV. The pattern of binding of each known NLV to the blood antigen can reveal the type of blood antigen present in the biological sample. In a preferred embodiment, the method comprises contacting separate saliva sample targets with NLV strains 387, MOH, NV, 02-1419, and 207, and detecting any complex of the NLV strain with blood antigen in the saliva samples. Table C shows the six binding patterns for the histo-blood group antigens with these five NLV strains when detecting with a NLV antibody, and the blood type of the biological sample that corresponds to the binding pattern.

TABLE C

Binding by NLV Antibody for a complexed NLV

| | Complexed NLV | | | | | Biological sample |
|---|---|---|---|---|---|---|
| Pattern no | 387 | NV | MOH | 02-1419 | 207 | Blood type |
| 1 | B | — | B | — | — | "B secretor" |
| 2 | B | B | B | B | — | "A secretor" |
| 3 | B | B | B | B | — | "AB secretor" |
| 4 | B | B | — | — | — | "O secretor" |
| 5 | — | — | — | — | B | "Non-secretor" |
| 6 | — | — | — | — | — | "Le$^-$, non-secretor" |

B = Binding by the NLV antibody
— = minimal or no binding

Since the original discovery of the prototype Norwalk Virus in the early 1970s, there has been a dramatic decrease in the outbreaks of the NV worldwide, to the point that a NV infection and outbreak are rare. The NLVs other than NV are more important from a human health standpoint. Consequently, preferred embodiments of the present invention include methods and kits that use, or that detect and identify, NLVs other than the Norwalk Virus.

The presence of a NLV, and its blood antigen specificity or binding pattern, can be determined by sampling a food or water suspected of being contaminated with a NLV, or by sampling a biological (usually, a stool sample) of a person suffering from symptoms of a NLV infection (such as vomiting and diarrhea), and assaying the food, water, or biological sample for the presence of a NLV. The method provides a means for detecting a NLV in a biological, water, and/or food sample suspected of containing a NLV, by contacting the biological sample with human histo-blood group antigens targets, or a functionally equivalent molecule thereof, and then detecting the NLV-blood antigen complex.

Antibody Detection Means:

Detectable anti-antigen antibodies that bind specifically to the antigen-determinant epitope of blood antigen(s) include: for an H antigen, BG-4; for an A antigen, BCR 9010; for a B antigen, BCRM 11007; for a $Le^a$ antigen, BG-5; and for a $Le^b$ antigen, BG-6. These are available from Signet Laboratories, Inc. (Dedham, Mass.) and Accurate Chemical & Scientific Corporation (Westbury, N.Y.).

Detectable anti-NLV antibodies, detectable NLV antibodies, detectable anti-antigen antibodies and detectable antigen antibodies can be detected, or made detectable, in several ways that are well known to one of ordinary skill in this art. For detection purposes, an antibody or antigen is, in general, linked to a molecule that emits a signal or catalyzes an enzymatic change in a substrate. In either case, a colorimetric read-out is obtained. In the case of catalysis of a substrate, the color change may be visible to the naked eye, and thus may be conveniently used when performing a few tests, typically less than 10-12. When an array of test samples are measured, the preferred spectrophotometric method is a microtiter plate reader, of which there are many commercially available models.

Another detectable antibody can comprise an antibody or antigen linked to a photochrome molecule that can be detected when viewed with an appropriate light wavelength and filter. For example, fluorescein isothyocyanate, phycoerythrin, Texas Red, or other fluorescent moieties may be covalently linked to antibody or antigen and detected spectrophotometrically. Another useful means of making a detectable antibody involves linking a catalyst horse-radish peroxidase (HRP) to an antibody or antigen to be detected, and visualizing by addition of a substrate solution. The resultant color change can be measured spectrophotometrically. A biotin-conjugated antibody is another useful detectable antibody form, which following incubation with streptavidin-fluorescein can be measured spectrophotometrically. A biotin-avidin complex can also be detected using commercially available kits. The biotin is linked to the antibody, then complexed with avidin linked to an enzyme that may be detected by staining. Vectastain™ ABC kit is an example of this staining technique.

a. Inhibiting the Binding Activity of a NLV Toward a Blood Antigen

The invention includes a method of identifying a first test compound that inhibits the binding activity of a NLV with a blood antigen. The method comprises the steps of:

contacting a NLV target with a first test compound;

contacting the NLV with a first standard compound that is known to bind with a determinant binding site of the NLV;

determining whether the binding of the first standard compound is decreased in the presence of the test compound, the decrease in binding being an indication that the first test compound inhibits the binding activity of the NLV toward the first standard compound.

The first standard compound that is known to bind with the determinant binding site of the NLV can be a native histo-blood antigen, selected from the group consisting of the ABH blood group antigens, the Lewis blood group antigens, and mixtures thereof. The ABH blood group antigens can be selected from H antigen, A antigen, B antigen and a mixture thereof, while the Lewis group antigens can be either the $Le^a$ (non-secretor) antigen or the $Le^b$ (secretor) antigen. The first standard compound can also comprise a synthetic oligosaccharide with one or more conjugated moieties having receptor binding properties that are functionally equivalent to those of the antigenic determinant epitopes of human histo-blood group antigens. Such compounds are known to have specific binding to human histo-blood antigens, and are commonly used for determining human blood type. Examples of such first standard compounds include A trisaccharide-BSA (GalNAc-α1→3 (Fuc-α1→2) Gal β-O-space) nBSA), B trisaccharide-BSA (Gal-α1→3 (Fuc-α1→2) Gal 3-O-space) nBSA), Lacto-N-fucopentaose II-BSA [or, $Lewis^a$ trisaccharide], Lacto-N-fucopentaose I-BSA [or H type 1 trisaccharide], and Lacto-N-difucohexaose I-BSA [or, $Lewis^b$ trisaccharide], available from Glycorex AB, Lund, Sweden, and from V-Labs, Inc., Covington, La.

The step of determining whether the binding of the first standard compound is decreased comprises the step of detecting the presence of the standard compound on the NLV target. The first standard compound can comprise a detectable linked molecule that can emit a signal or catalyze an enzymatic change in a substrate. The first standard compound can also be detected by contacting the NLV target with a detection compound, such as a detectable antibody, which selectively binds to the standard compound, and then detecting the antibody.

A control test is also conducted to detect the binding of the first standard compound with the NLV target without precontacting of the first test compound. The detection value for the test leg is then compared with the detection value for the control leg to determine whether the binding of the first standard compound had decreased in the presence of the first test compound.

The first test compound is preferably selected from the group consisting of a protein, a polypeptide, an oligosaccharide, another histo-blood group antigen, a natural or synthetic compound, and a poly- and monoclonal antibody. An oligosaccharide is a preferred compound, since it is generally regarded as safe. A monoclonal antibody to the determinant binding site of the NLV can be prepared, and isolated by procedures that are well known to those skilled in the art. The first test compound can also be a molecularly-engineered compound that is designed to have a binding site geometry that is complimentary to the determinant binding site of the NLV.

A first compound that can competitively bind with a NLV and thereby prevent a blood antigen from binding can also be selected based on a mimicking of the chemical structure, geometry, or binding specificity of the antigenic-determinant epitope of a human histo-blood antigen that is known to bind with the determinant binding site of the particular NLV.

A first test compound of the present invention can be selected from compounds that have the same, or substantially the same, chemical structure as the human histo-blood group antigen's antigenic determinant epitope. The antigenic determinant epitope of the H antigen comprises the Fuc-α1→2 structure. The antigenic determinant epitope of the A antigen comprises the GalNAc-α1→3 structure. The antigenic determinant epitope of the B antigen comprises the Gal-α1→3 structure. The antigenic determinant epitope of the $Le^a$ antigen comprises the Fuc-α1→3/4 structure(s). The antigenic determinant epitope of the $Le^b$ antigen comprises the Fuc-α1→2 structure. A preferred compound is a synthetic or natural oligosaccharide that comprises one or more moieties selected from the structures Fuc-α1→2, GalNAc-α1→3, Gal-α1→3, Fuc-α1→3/4, and mixtures thereof. Preferably the compounds is a carbohydrate selected from the group consisting of fucosyl α1→3/4 N-acetyl glycosyl globoside (F3AG), a stabilized, synthetic F3AG analogue, and mixtures thereof, in an amount that inhibits binding of NLV strain 207 to gastroepithelium of a non-secretor individual; a carbohydrate selected from the group consisting of fucosyl α1→2 galactose globoside (F2G), a stabilized, synthetic F2G analogue, and mixtures thereof, in an amount that inhibits binding of NLV strain 387 to gastroepithelium of a secretor individual; a carbohydrate selected from the group consisting of N-acetyl galactosyl α1→3 galactosyl globoside (AG3G), N-acetyl galactosyl α1→4 galactosyl globoside (AG4G), a stabilized, synthetic AG3G analogue, a stabilized, synthetic AG4G analogue, and mixtures thereof, in an amount that inhibits binding of NLV strain MOH to gastroepithelium of a secretor individual; and a carbohydrate selected from the group consisting of galactosyl α1→3 galactosyl globoside (G3G), galactosyl α1→4 galactosyl globoside (G4G), a stabilized, synthetic G3G analogue, a stabilized, synthetic G4G analogue, and mixtures thereof, in an amount that inhibits binding of NLV strain MOH to gastroepithelium of a secretor individual.

A first test compound can also be selected from compounds that have the same geometric structure as the human histo-blood group antigen's antigenic determinant epitope. The nucleotide and amino acid sequences of the NLV capsid genes of several NLV strains, and the three-dimensional structure of the prototype NV, are known, and could be used to model ligand-receptor (binding site-epitope) interaction for the engineering of such compounds.

A first test compound can also be selected from a compound that has the binding specificity of the antigenic determinant epitope of a blood antigen, and functionally equivalent molecules thereof. Such compounds can include monoclonal antibodies. A preferred antibody is an anti-antibody to the antigenic determinant epitope. An example of such an antibody is the 9C3 Mab that can bind at the determinant binding site of the NV with the binding specificity of the antigenic determinant epitope of the H-type blood antigen, and is available from Dr. Xi Jiang, Children's Hospital Research Center, Cincinnati, Ohio.

b. Inhibiting the Binding Activity of a Blood Antigen Toward a NLV

The invention includes a method of identifying a second test compound that inhibits the binding activity of a blood antigen with a NLV. The method comprises the steps of:

contacting a histo-blood group antigen target with a second test compound;

contacting the blood antigen with a second standard compound that is known to bind with an antigenic determinant epitope of the blood antigen;

determining whether the binding of the second standard compound is decreased in the presence of the second test compound, the decrease in binding being an indication that the second test compound inhibits the binding activity of the blood antigen toward the second standard compound.

The second standard compound that is known to bind with the antigenic determinant epitope of the blood antigen can be a recombinant NLV that retains the VLP shape and structure of the wild-type NLV, but has been rendered reproductively inert by molecular engineering methods known to those skilled in the art.

The step of determining whether the second binding of the standard compound is decreased comprises the step of detecting the presence of the second standard compound on the blood antigen target. The second standard compound can comprise a detectable linked molecule that can emit a signal or catalyze an enzymatic change in a substrate. The second standard compound can also be detected by contacting the blood antigen target with a detection compound, such as a detectable antibody, which selectively binds to the second standard compound, and then detecting the antibody.

A control test is also conducted to detect the binding of the second standard compound with the blood antigen target without pre-contacting of the second test compound. The detection value for the test leg is then compared with the detection value for the control leg to determine whether the binding of the second standard compound had decreased in the presence of the second test compound.

The second test compound is preferably selected from the group consisting of a protein, an oligosaccharide, another histo-blood group antigen, a natural compound, and a monoclonal antibody. An oligosaccharide is a preferred compound, since it is generally regarded as safe. A monoclonal antibody to the antigenic determinant epitope of the blood antigen can be prepared, and isolated by procedures that are well known to those skilled in the art. The second test compound can also be a molecularly-engineered compound that is designed to have a binding site geometry that is complimentary to the antigenic determinant epitope of the blood antigen.

The invention also includes a hybridoma that can produce a monoclonal antibody as a second test compound, made constructed by a means well known in the art.

A second test compound that can competitively bind with a blood antigen and thereby prevent a NLV from binding can also be selected based on a mimicking of the chemical structure, geometry, or binding specificity of the determinant binding site of a NLV that is known to bind with the antigenic determinant epitope of the particular blood antigen.

A second test compound of the present invention can be selected from compounds that have the same, or substantially the same, chemical structure and/or geometric structure as the NLV's determinant binding site. The nucleotide and amino acid sequences of the NLV capsid genes of several NLV strains, and the three-dimensional structure of the prototype NV, are known, and could be used to model ligand-receptor (binding site-epitope) interaction for the engineering of such compounds.

A second test compound can also be selected from compounds that have the binding specificity of the NLV's determinant binding site.

c. Other Embodiments of the Invention

The invention also includes a medicament and a pharmaceutical composition comprising an active compound selected from the group consisting of a first test compound, a second test compound, and a mixture thereof; and a pharmaceutically acceptable diluent, carrier or excipient. A preferred composition comprises at least one, and preferably two or more, first test compounds that can prevent the host blood antigen from binding with any NLV in vivo, thereby inhibiting an infection, or treating an infection, of the host by the NLV. Preferably, the first test compounds prevent any host blood antigen selected from the ABO blood type antigens, and the Lewis blood antigens, from binding with any NLV in vivo Non-limiting examples of suitable pharmaceutically acceptable carriers include phosphate buffered saline solutions, water, emulsions including oil/water emulsions, various types of wetting agents such as detergents, and sterile solutions. Compositions comprising such carriers can be formulated by well known conventional methods. Compositions can also comprise liquid or viscous compositions that can coat and/or line the surface of the GI tract, thereby placing the active compounds in direct proximity with the epithelial cells.

The invention also relates to a method for preventing an infection of a host by a NLV, by administering to the host an effective preventative amount of a prevention compound that inhibits binding of the NLV in vivo to a histo blood group antigen of the host. The invention can also relate to a method for treating an active infection of a host by a NLV, by administering to the host an effective treatment amount of a treatment compound that inhibits binding of the infecting NLV in vivo to a histo blood group antigen of the host.

The invention further relates to a use of a preventative compound in a medicament or pharmaceutical for the prevention and treatment in a mammal of an infection by a NLV, wherein the preventative compound has the binding specificity of the antigenic determinant of a human histo-blood group antigen.

The prevention compound can be selected from the first test compound, the second test compound, or a mixture thereof. The treatment compound can be selected from the first test compound, the second test compound, or a mixture thereof.

Preferred are medicaments and pharmaceutical compositions comprising at least one of, though typically a plurality of, a prevention or treatment compound, which can bind with any infecting strain of NLV. When an outbreak of a NLV occurs, the time to isolate and detect the specific strain of NLV for pinpoint treatment can delay administration of treatment or prevention compositions to a population of infected or susceptible persons. Preferably, a combination of treatment or prevention compounds in a single medicament or pharmaceutical that can singularly or jointly bind with any strain of NLV, will ensure effective treatment or prevention of infection, regardless of the particular strain(s) of virus involved.

The effective prevention amount of the prevention compound is an amount sufficient to bind any NLV that is present in the gastrointestinal system of a host who had consumed a food or water source contaminated by the NLV. Ordinarily, these amounts of NLV would be very low. For this reason, a preferred prevention compound is a first test compound that binds with the NLV to prevent its further binding with the host blood antigens. The amount of the prevention compound to be consumed will typically range from about 100 to about 10,000 units per dose, more preferably from about 1,000 to about 10,000 units per dose, where a unit defines the amount of the compound to bind with a single virus particle. Preferably, according to the method of the invention, a dose of the medicament comprising the compound would be consumed by the host just prior to, while, or just after, consuming a food or water suspected of being contaminated with a NLV.

The effective treatment amount of the treatment compound is an amount sufficient to bind any NLV that are progeny from those infected within the epithelial cells of the gastrointestinal system of a host. Ordinarily, these amounts of NLV would be high compared to amounts of NLVs found in a contaminated water or food. The amount of the treatment compound to be consumed will typically range from about 1,000 to about 100,000 units per dose, more preferably from about 10,000 to about 100,000 units per dose, where a unit defines the amount of the compound to bind with a single virus particle. Preferably, according to the method of the invention, a dose of the medicament comprising the compound would be consumed by the host periodically until the symptoms of the infection have dissipated and stopped. Since any consumed treatment compound would pass through the gastrointestinal system in the ordinary course, the periodic dosage is preferably about every 1 to 4 hours.

EXAMPLES OF THE INVENTION

Example 1

A test was conducted to measure the binding by one or more recombinant NLV with blood antigens in human saliva samples.

Human subject phenotypes: The human subjects' phenotypes of histo-blood group antigens were determined by EIAs using monoclonal antibodies specific to $Le^a$, $Le^b$, A, B and H blood group antigens. Salivary anti-NLV IgA was determined by EIAs using recombinant NLV capsids as coating antigens.

Saliva samples were diluted at 1:1,000 in PBS and then coated onto microtiter plates (Dynex Immulon) overnight at 4° C. After blocking with 5% Blotto, monoclonal antibodies specific to Lewis a, Lewis b, H type 1, type A, and type B antigens were added. MAbs BG-4 anti-H type 1, BG-5 anti-$Le^a$, and BG-6 anti-$Le^b$ were purchased from Signet Pathology Systems (Dedham, Mass.). MAbs BCR9031 anti-H type 2, BCR 9010 anti-A, and BCRM 11007 anti-B were purchased from Accurate Chemical & Scientific Corporation (Westbury, N.Y.). After incubation for 1 hour at 37° C., HRP-conjugated goat anti-mouse IgG or IgM antibodies were added. Following each step, the plates were washed 5 times with PBS. The color reaction was developed and recorded as described above.

Of the 54 human subjects, 11 (20%) were $Le^+$/non-secretors, 36 (67%) were $Le^+$/secretors, and 7 (13%) were $Le^-$ individuals. Among the 7 $Le^-$ individuals, 6 were secretors and one was a non-secretor. Of the 54 individuals, 17 (32%) were type A, 4 (7%) were type B, 33 (61%) were type O, and none were type AB.

Recombinant NLV Capsid:

Baculovirus-expressed recombinant capsid proteins of five NLVs were prepared by methods disclosed in the art: one virus of genogroup I NLVs (NV) and three viruses of genogroup II NLVs (207, 387, 02-1419, and MOH).

Procedure:

The recombinant viral capsid protein of each of the five NLVs was tested by enzyme immune assays (EIAs) for the ability to bind to blood antigens in saliva samples of each human subject. The saliva samples were boiled and centrifuged, and the supernatant stored frozen until use. For testing recombinant NLV (rNLV) binding to saliva, microtiter plates (Dynex Immulon, Dynatech) were coated with the saliva samples at a dilution of 1:5,000 in phosphate buffer saline (PBS). After blocking in 5% dried milk (Blotto), the rNLV capsid proteins at ~1.0 μg/ml in PBS were added. The bound rNLV capsid proteins were detected using a pooled guinea pig anti-NLVs antiserum for the respective NLV, followed by addition of horseradish peroxidase (HRP)-conjugated goat anti-guinea pig IgG (ICN, Aurora, Ohio). In each step, the plates were incubated for 1 hour at 37° C. and washed five times with PBS. The enzyme signals were detected by the TMB kit (Kirkegard & Perry Laboratories, Gaithersburg, Md.) then read at a wavelength of 450 nm using an EIA spectra reader (Tecan, Durham, N.C.) as described by the manufacturers.

Figure 2:
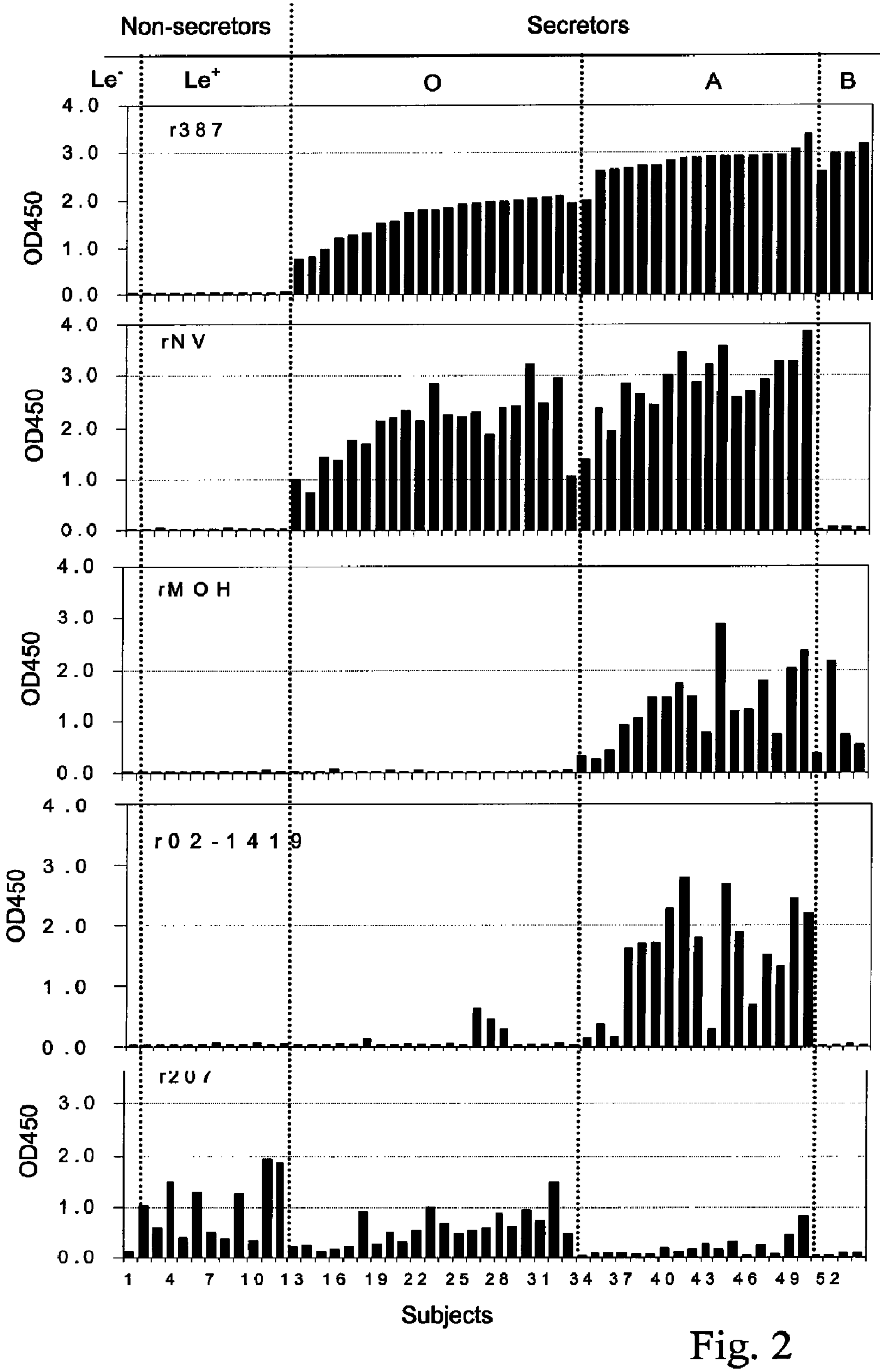
FIG. 2 shows graphic results of the binding strength of five NLVs based on the histo-blood phenotypes for secretors (A, B and O blood types) and non-secretors ($Le^-$ and $Le^+$).
Figure 3:
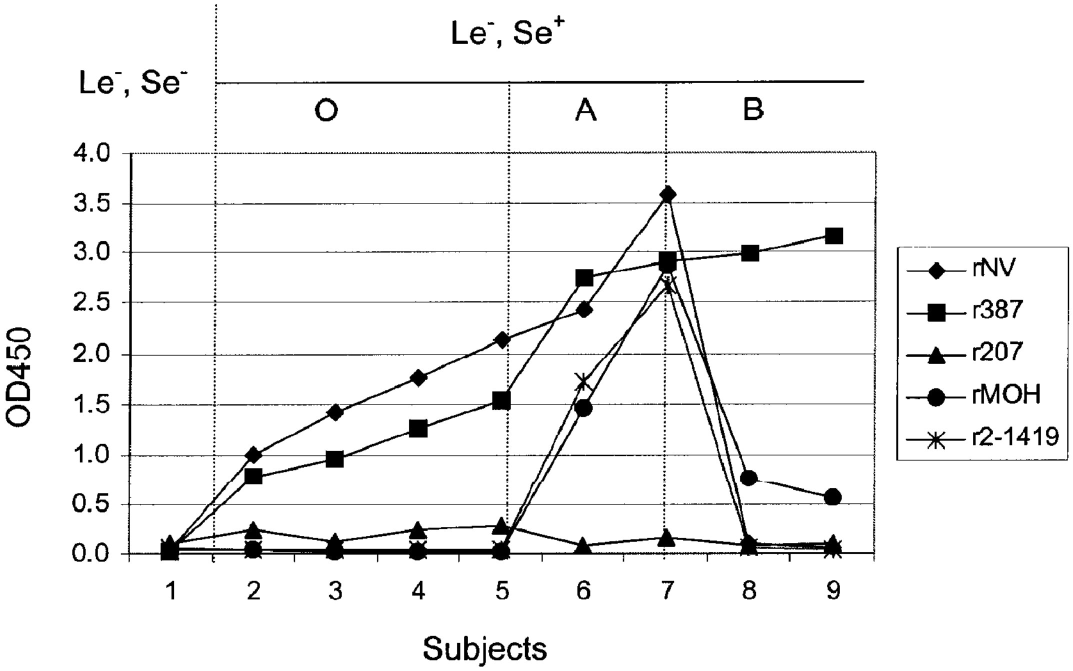
FIG. 3 shows graphic results of the binding strength of five NLVs based on histo-blood phenotype of Lewis negative ($Le^-$) secretors (A, B and O blood types) and non-secretors.

The results are shown in FIGS. 2 and 3. FIG. 2 shows graphic results of the binding strength of the five NLVs based on the histo-blood phenotypes for secretors (A, B and O blood types) and non-secretors ($Le^-$ and $Le^+$) for the 54 human subjects. FIG. 3 shows graphic results of the binding strength of the five NLVs based for the 9 Lewis negative ($Le^-$) subjects with histo-blood phenotypes secretors (A, B and O blood types) and non-secretor.

Without being bound to any particular theory, these results and the known biosynthetic pathways for human histo-blood group antigens show that certain virus strains appear to recognize specific determinant epitopes on the histo-blood group antigens. Strain 207 apparently recognizes $Le^a$ antigen, as $Le^a$ is the only antigen found in the saliva of Lewis-positive non-secretor individuals. Secretor individuals also can make $Le^a$ antigens, although at smaller amounts in saliva as compared to other blood antigens, due to the presence of 1,2 fucosyltransferase expressed by the secretor gene (FUT2). Thus 207 virus binds at minimal levels and with less avidity to the saliva of secretors than to non-secretors. Variable expression of the FUT2 fucosyltransferase in secretors may account for the lack of a clear demarcation between 207 binders and non-binders. Strain 207 did not bind to blood antigens in the saliva from Lewis-negative individuals who lack FUT3 and thus do not make $Le^a$ antigen. VA207 also recognizes $Le^x$ that is the product of the FUT3 enzyme on the type 2 molecules.

The histo-blood group antigens in the saliva of secretor individuals are more complex due to the interactions between the ABO, Lewis, and secretor genes. Strain 387 has a broad specificity, possibly binding all fucosylated antigens in secretors; similarly, NV binds all fucosylated antigens except for type B. MOH is predicted to recognize type A and type B antigens but not H and $Le^b$ antigens, because MOH reacted with types A and B but not with type O. Strain 02-1419 appears to bind type A antigen, but not the H, B, $Le^b$ and $Le^a$ antigens, because 02-1419 strain reacted with type A but not with types B or O. These four secretor-binding strains also recognize H type 2, $Le^y$, A type 2 and B type 2, A $Le^y$, and B $Le^y$, because these are the product of the FUT2 enzyme on the type 2 molecules. The Lewis epitope, i.e., moieties containing α1,4 fucose in Lewis-positive secretors, does not appear important for binding by MOH, 387, NV, and 02-1419, because these strains bind to saliva from Lewis-negative secretors, who lack this epitope. The presence of the Lewis epitope did not affect viral binding to other epitopes; therefore, the antigens in secretor individuals that bind MOH, 387, 02-1419, or NV are probably limited to the H, A, and B antigens.

Example 2

A test is conducted to demonstrate that the binding of a NLV to a blood antigen in its natural binding pattern is inhibited and prevented, by contacting the NLV with a compound known to bind to the determinant binding site in the NLV capsid.

The Norwalk Virus (NV) is known to bind with the H antigen and the A antigen (that is, these antigens are in its binding pattern). Recombinant NV capsid protein at ~1.0 μg/ml in PBS is coated into the well(s) of a microtiter plate (Dynex Immulon, Dynatech). After blocking, a MAb 9C3, known to bind to the determinant binding site of the NV, is applied to a first group of the NV targets. A second group of the NV targets are left untreated. After incubation, the first set of NV targets is washed five times with PBS. Saliva from a person of secretor-A phenotype is prepared as in Example 1, and is applied to both the first and second groups of NV targets. After incubation, both groups of NV targets are detected with an A-antigen antibody to detect the presence of A antigen on the NV targets. The first group of NV targets shows no A antigen, while the second group of NV targets shows significant A antigen from the saliva sample binding to the NLV.

We claim:

1. A method for treating an active Norwalk-Like Virus (NLV) infection in the gastrointestinal (GI) tract of a host who consumes a food or water source contaminated with the NLV, comprising the steps of:

a. providing a medicament or pharmaceutical comprising a compound having the binding specificity of the antigenic determinant of a human histo-blood group antigen, the compound being at least one carbohydrate compound that competitively binds with a NLV at the determinant binding site of the NLV, the at least one carbohydrate compound selected from the group consisting of:

1) at least one carbohydrate selected from the group consisting of fucosyl α1→3/4 N-acetyl glycosyl globoside (F3AG), in an amount that inhibits binding of NLV strain 207 to gastroepithelium of a non-secretor individual;

2) at least one carbohydrate selected from the group consisting of fucosyl α1→2 galactose globoside (F2G), in an amount that inhibits binding of NLV strain 387 to gastroepithelium of a secretor individual;

3) at least one carbohydrate selected from the group consisting of N-acetyl galactosyl α1→3 galactosyl globoside (AG3G), N-acetyl galactosyl α1→4 galactosyl globoside (AG4G), and mixtures thereof, in an amount that inhibits binding of NLV strain MOH to gastroepithelium of a secretor individual;

4) at least one carbohydrate selected from the group consisting of galactosyl α1→3 galactosyl globoside (G3G), galactosyl α1→4 galactosyl globoside (G4G), and mixtures thereof, in an amount that inhibits binding of NLV strain MOH to gastroepithelium of a secretor individual; and 5) mixtures thereof; and b. administering orally the medicament or pharmaceutical to a host that has a NLV infection from consuming a food or water source contaminated with the NLV, in an effective amount of the compound sufficient to inhibit binding of the NLV in vivo to a histo blood group antigen in the GI tract of the host, which inhibits the active infection of the GI tract of the host by the NLV that contaminates the consumed food or water source.

2. The method according to claim 1, wherein the step of administering comprises consuming by the host of a dose of the compound while consuming the food or water source.

3. The method according to claim 1 wherein the effective amount is an effective treatment amount of the compound, which inhibits the active infection by the NLV of the host.

4. The method according to claim 3, wherein the step of administering comprises consuming by the host of at least one dose of the compound while experiencing the symptoms of infection by the NLV.

5. The method according to claim 4, wherein the effective treatment amount is from about 1,000 units to about 100,000 units per consumed dose.

6. The method according to claim 5, wherein the effective treatment amount is from about 10,000 units to about 100,000 units per consumed dose.

7. The method according to claim 6 wherein the at least one dose is a plurality of doses administered periodically about every 1 to 4 hours.

* * * * *

UNITED STATES PATENT AND TRADEMARK OFFICE

CERTIFICATE OF CORRECTION

PATENT NO. : 8,026,221 B2
APPLICATION NO. : 12/040530
DATED : September 27, 2011
INVENTOR(S) : Xi Jiang et al.

It is certified that error appears in the above-identified patent and that said Letters Patent is hereby corrected as shown below:

In the Specification

Column 1, lines 19-24 should read

-- This invention was made with government support under HD013021 and AI037093 awarded by the National Institutes of Health. The government has certain rights in the invention. --

Signed and Sealed this
Twenty-fifth Day of June, 2013

Teresa Stanek Rea
*Acting Director of the United States Patent and Trademark Office*